US00PP10079P

United States Patent [19]

Hanna

[11] Patent Number: Plant 10,079

[45] Date of Patent: Oct. 21, 1997

[54] 'TIFT 94' BERMUDAGRASS

[75] Inventor: Wayne William Hanna, Chula, Ga.

[73] Assignee: The United States of America as represented by the Secretary of Agriculture, Washington, D.C.

[21] Appl. No.: 634,149

[22] Filed: Apr. 19, 1996

[51] Int. Cl.[6] ..... A01H 5/00

[52] U.S. Cl. ..... Plt./90

[58] Field of Search ..... Plt./90

[56] References Cited

PUBLICATIONS

B. Sigurbjörnsson, "Chapter 8 Induced Mutations" *Crop Breeding*, 1983 ASACSSA, Madison, Wi., pp. 153–176.

*Primary Examiner*—James R. Feyrer

*Attorney, Agent, or Firm*—M. Howard Silverstein; C. Andrew Watkins; John D. Fado

[57] ABSTRACT

Tift 94 is a vigorous triploid (2n=3x=27 chromosomes) which has use on golf course fairways and tees, athletic fields, lawns, commercial landscape sites, and other turf areas where a fine-textured, low growing turf is desired. The grass produces less upright growth and has shorter and narrower leaves, and shorter internodes than Midiron from which it was developed and Tifway, two commercially available cultivars. It produces more shoots per node than Midiron. It has better color and turf quality than Midiron.

3 Drawing Sheets

BACKGROUND OF THE NEW VARIETY

Bermudagrass, *Cynodon dactylon* (L.) Pers. is a warm-season perennial sod-forming grass that spreads by stolons and rhizomes. Bermudagrass probably originated from Africa and South and Southeast Asia but it has been introduced to all tropical and subtropical regions of the world.

The species has been observed to survive at 50° N in Europe and to 4000 m elevation in the Himalayas. It is also found on islands in the Pacific, Atlantic and Indian Oceans.

Roots and rhizomes of this species can penetrate the soil to a depth of 1 m or more. A large amount of morphological variability exists in this species.

Both common and triploid hybrid types are used for turf. Common types have 2n=18 or 36 chromosomes and produce seeds. Triploid hybrids have 2n=3x=27 chromosomes and are male and female sterile. Both can be propagated by stolons and/or rhizomes. Only common bermudagrass types can be propagated by seeds.

Bermudagrass can be used to produce an attractive wear-resistant turf if managed properly. Midiron is a medium coarse 2n=3x=27 chromosome hybrid released by the Kansas Agricultural Experiment Station in 1971 for use in USDA plant hardiness zone 6 (USDA Agricultural Handbook 170). It is reported to be an interspecific cross between a *C. dactylon* selection (used as female) from N. Platte, Nebr. and Ugandagrass (*C. transvaalensis*) as male. Tifway is a fine 2n=3x=27 chromosome hybrid released by the USDA-ARS and the Georgia Coastal Plain Experiment Station in 1960. Tifway is adapted to USDA plant hardiness zones 7, 8, 9 and 10 and similar areas around the world. Tifway is planted on a larger area around the world than any other improved triploid turf bermudagrass because of its dark green color, fineness, wear-resistance and persistence. However, Tifway does not survive reliably in USDA plant hardiness zone 6 and in the northern half of zone 7. Midiron is much coarser than Tifway and does not produce as high quality turf.

The popularity of Tifway produces a potential genetic vulnerability problem in that a single vegetatively propagated genotype is planted over a large area. Development of genetically different fine-textured genotypes would lessen the threat of the industry having a suitable grass to plant if one genotype suddenly became susceptible to a pest.

It was anticipated that Tifway 2 (released in 1991) would become a more popular cultivar to plant than Tifway. However, Tifway continues to be the most popular cultivar for fairways, tees, athletic fields, lawns and recreational areas because it performs as well or better than Tifway 2 under most circumstances.

Mutagens have been used to induce dwarfness in numerous crops. An induced fine-textured mutant in Midiron would combine winterhardiness and high turf quality in another genotype.

BRIEF DESCRIPTION OF THE PHOTOGRAPHS

SUMMARY OF THE INVENTION

Figure 1:
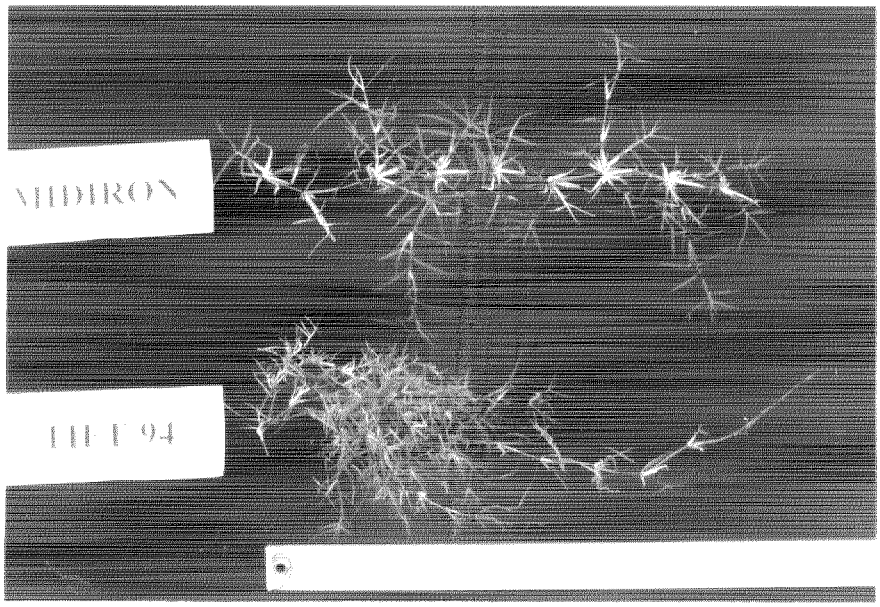
FIG. 1 is a photograph of 40 day old stolon growth of Tift 94 and Midiron (the commercial cultivar from which Tift 94 was developed) showing the fine texture due to shorter and narrower leaves and shorter internodes of Tift 94.
Figure 3:
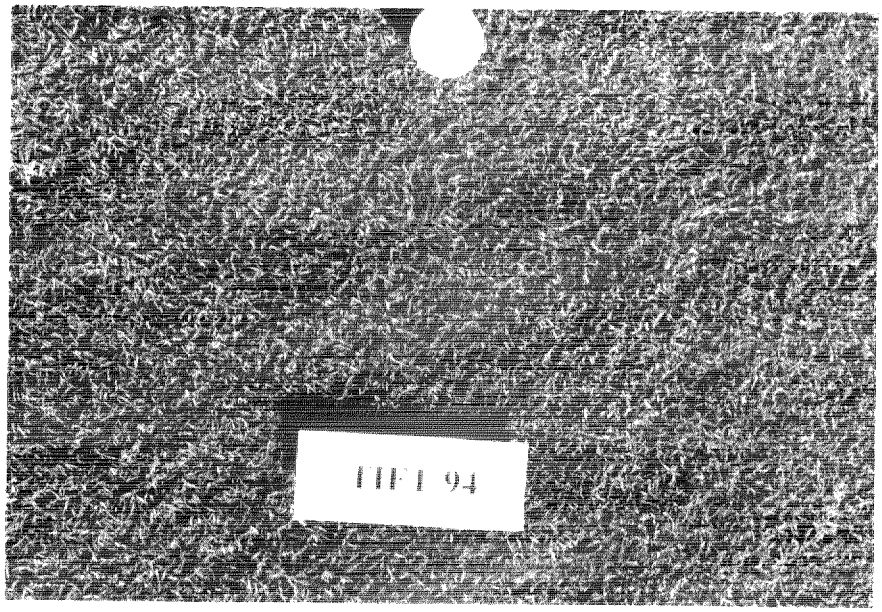
FIG. 3 is a photograph of Tift 94 mowed at 12 mm three times per week showing the dense high quality turf produced by this cultivar.
Figure 2:
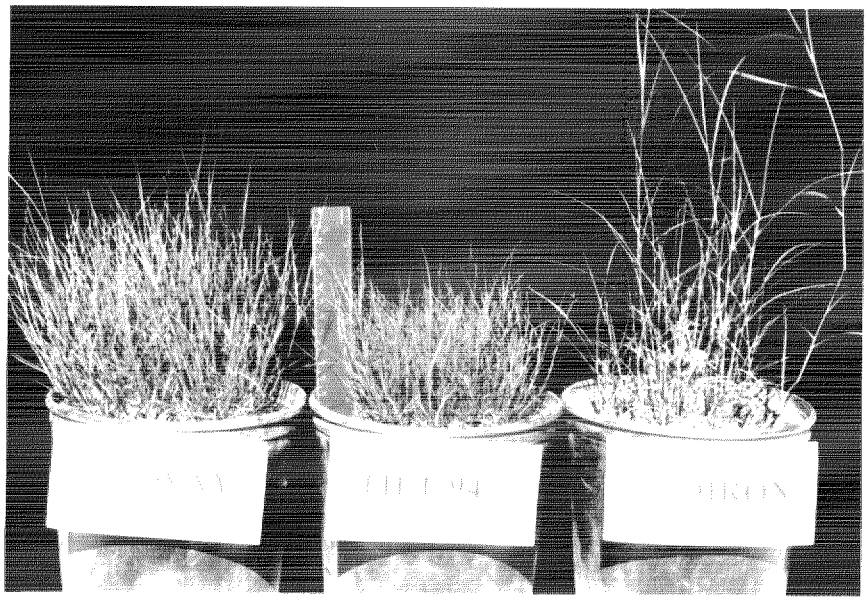
FIG. 2 is a photograph of thirty-two day shoot growth from 10 cm sod plugs of Tift 94, Midiron and Tifway in the greenhouse showing the shorter shoot growth of Tift 94 and the higher density of shoots from Tift 94 compared to Midiron.

Tift 94 is a vigorous triploid (2n=3x=27 chromosomes) which has use on golf course fairways and tees, athletic fields, lawns, commercial landscape sites, and other turf areas where a fine-textured, low growing turf is desired. The grass produces less upright growth and has shorter and narrower leaves, and shorter internodes than Midiron from which it was developed and Tifway, two commercially available cultivars. It produces more shoots per node than Midiron. It has better color and turf quality than Midiron.

DETAILED DESCRIPTION OF THE PLANT

Bermudagrass Tift 94 is a fine-textured mutant selected 'om plants established from dormant stolons of the Midiron ultivar of *Cynodon dactylon* (L.) Pers.×*C. transvaalensis* lutt-Davy treated with 8000 rads of Cobalt 60 gamma adiation on Jan. 20, 1983. Dormant stolons of Midiron were btained from Ralph White of Southern Turf Nursery. Radiation treated stolons were planted in steam-sterilized oil in flats in the greenhouse immediately after treatment. Sixty-six fine-textured mutants or sectors were selected on stolons, separated from the stolon and individually propagated. Tift 94 was one of the 66 single plant selections and was tested as MI40 in tests in Tifton, Ga.; Stillwater, Okla.; Lexington, Ky.; and Lake Wales, Fla.; Ft. Bluff, Tenn. and Lincoln, Nebr.

Tift 94 is a finer-textured mutant induced with radiation in the Midiron cultivar of bermudagrass. It has 2n=3x=27 chromosomes like Midiron. Initially at Tifton, Ga., 'Tift 94' has been vegetatively propagated by shoots, stolons or rhizomes through plugging, sprigging and sodding. Tift 94 is a single genotype that produces a uniform turf. It has been propagated true-to-type from 1983 to 1995.

Tift 94 has been evaluated in 12 experiments at six locations. In all experiments except at Stillwater, Okla., the Bermudagrass entries were replicated and the data analyzed statistically. Significant refers to the P=0.05 probability level.

After eight years of mowing three times per week at a 25 mm height, Tift 94 produced significantly better quality turf (8 on scale where 9 is best) than Midiron (5.8) under medium fertility and management. In another test, mowed three times per week at 12 mm for six years, Tift 94 averaged an 8.4 turf quality rating while Midiron was rated 2.6. The fine-textured characteristics of Tift 94 allows it to produce better quality turf under close (12 mm and 25 mm) and frequent cutting. Compared to Tifway and Tifway 2, Tift 94 had similar or slightly higher turf quality ratings.

Based on color ratings, Tift 94 was significantly greener than Midiron in April, November, December and January. Tift 94 began growing (greenup) earlier than Midiron in 1993 but not in 1991. Color ratings for Tift 94, Tifway and Tifway 2 are similar.

In the fall of 1993, Tift 94 plots had fewer mole crickets than most of the major commercial turf cultivars. No differences were observed in mole cricket ratings. between Tift 94 and Tifway in 1995; both showed low (0.5) infestation on a scale of 1 to 5 (where 5 is severe).

Tift 94 has produced good quality turf as far north as Lexington, Ky.; Stillwater, Okla.; and Ft. Bluff, Tenn. and as far south as Lake Wales, Fla. Tift 94 was the only one of six midiron mutants planted at Lincoln, Nebr. that survived the 1990–91 winter.

Tift 94 establishes at about the same rate as Tifway and Tifway 2.

Shoot growth (thirty-two days) from 10 cm plugs growing in the greenhouse in October was 10.7 cm tall for Tift 94 and 20.6 cm and 14.9 cm for Midiron and Tifway, respectively. Leaf length was shorter (5.6 cm) for Tift 94 compared to 10.7 cm for Midiron and 7.0 cm for Tifway. Leaves of Tift 94 were narrower (1.2 mm) compared to 2.2 mm for Midiron and 1.4 mm for Tifway. More than five times as many shoots were produced from a 10 cm plug of Tift 94 (475) compared to 87 for Midiron.

In a three year old sod mowed weekly at 3 cm, internode lengths of horizontal stolons and vertical shoots were shorter for Tift 94 (1.2 cm and 0.6 cm, respectively) than for Midiron (2.5 cm and 1.0 cm) and Tifway (1.5 cm and 0.8 cm). Tift 94 also had shorter and narrower leaves (1.5 cm and 1.2 mm, respectively) than Midiron (2.0 cm and 1.9 m/m) and Tifway (1.6 cm and 1.2 mm).

Internode length of stolons in a juvenile growth stage on 40 day old plants in the field were in general similar for Tifton 94, Midiron and Tifway. The fourth and fifth internodes were shorter for Tift 94 and Midiron (22 or 23 mm) compared to Tifway (26 mm). Shoot numbers per node were similar for Tift 94 (1.2 to 2.7) and Tifway (1.2 to 2.6) but higher than for Midiron (1.0 to 1.5). Leaf length of Tift 94 was shorter (1.4 cm) than that of Midiron (1.9 cm) and Tifway (1.7 cm). Leaf width was the same for Tift 94 and Tifway (1.7 mm) but narrower than Midiron (2.3 mm).

TABLE 1

1991 ratings† on turf bermudagrass (Midiron mutants) established 8-25-83 at Tifton, GA‡.

| | Quality | |
|---|---|---|
| Cultivar‡ | 8/14 | 10/6 |
| Tift 94 | 8.0 | 8.0 |
| Midiron | 6.0 | 5.5 |
| LSD (.05) | 1.6 | 1.6 |

†Quality: 1 = poor, 9 = best
‡The best of 66 entries in the test. Plots were cut 3x each week at 25 mm from 1984 to 1991 and received 560 kg/ha 5-10-15 and 100 kg/ha N in March of each year. Plots were watered to prevent moisture stress.

TABLE 2

Ratings† on bermudagrass cultivars established 6-26-87 at Tifton, GA‡.

1991 Ratings

| | Quality | | | | | |
|---|---|---|---|---|---|---|
| Cultivar | 5/31 | 7/13 | 8/14 | 10/6 | 11/5 | x |
| Tift 94 | 8.0 | 7.5 | 7.0 | 8.5 | 9.0 | 8.0 |
| (Tifway)■ | (7.5) | | (6.5) | (7.5) | (7.5) | (7.3) |
| Tifway 2 | 8.0 | 5.5 | 6.5 | 7.5 | 7.5 | 7.0 |
| Midiron | 4.0 | 3.5 | 2.5 | 4.0 | 4.0 | 3.6 |
| LSD (0.05) | 0.9 | 1.9 | 1.5 | 2.0 | 1.8 | 1.6 |

| | Greenup | Color | |
|---|---|---|---|
| Cultivar | 3/28 | 10/6 | 11/5 |
| Tift 94 | 2.0 | 9.0 | 4.5 |
| (Tifway)■ | | (5.0) | (5.0) |
| Tifway 2 | 2.5 | 9.0 | 4.5 |
| Midiron | 2.0 | 3.0 | 2.0 |
| LSD (0.05) | 1.3 | 1.0 | 0.9 |

1992 Ratings

| | Quality | | | | | | |
|---|---|---|---|---|---|---|---|
| Cultivar | 5/1 | 6/18 | 8/4 | 9/1 | 9/25 | 11/23 | x |
| Tift 94 | 8.5 | 8.0 | 7.0 | 9.0 | 9.0 | 8.4 | |
| (Tifway) | (6.0) | (7.5) | (6.0) | (8.0) | (8.0) | (7.5) | (7.2) |
| Tifway 2 | 7.0 | 8.0 | 6.0 | 8.0 | 7.5 | 8.0 | 7.4 |
| Midiron | 2.5 | 4.0 | 2.0 | 3.5 | 2.5 | 2.5 | 2.8 |
| LSD (0.05) | 1.6 | 1.2 | 2.0 | 1.6 | 1.8 | 1.3 | 1.6 |

TABLE 2-continued

| Cultivar | Color 11/23 | 12/4 | 12/10 | 11/94 |
|---|---|---|---|---|
| Tift 94 | 4.0 | 4.0 | 3.0 | 3.0 |
| (Tifway) | | (4.0) | | (2.0) |
| Tifway 2 | 4.0 | 3.5 | 3.0 | 3.0 |
| Midiron | 2.0 | 1.5 | 1.0 | 1.0 |
| LSD (0.05) | 1.3 | 0.9 | 0.7 | 0.9 |

| Cultivar | Green-up 3/30 | 1993 Ratings: Color 4/23 | Color 12/17 | Quality 4/.23 | 6/9 | 7/16 | 9/16 | 10/19 |
|---|---|---|---|---|---|---|---|---|
| Tift 94 | 2.0 | 8.1 | 5.5 | 8.0 | 8.0 | 8.0 | 8.5 | 8.5 |
| (Tifway) | | (4.3) | | (7.5) | (6.0) | (6.0) | (7.0) | |
| Tifway 2 | 2.0 | 6.3 | 5.0 | 6.5 | 6.0 | 8.0 | 7.0 | 7.0 |
| Midiron | 1.0 | 3.6 | 3.5 | 3.0 | 3.0 | 2.5 | 2.5 | 2.5 |
| LSD (0.05) | 0.8 | 2.2 | 2.0 | 2.1 | 2.5 | 1.9 | 2.2 | 2.4 |

| Cultivar | 11/23 | 12/17 | x | Mole Cricket Damage 10/20 | 12/17 |
|---|---|---|---|---|---|
| Tift 94 | 8.5 | 9.0 | 8.4 | 1.0 | 1.0 |
| (Tifway) | | (8.0) | (6.5) | | |
| Tifway 2 | 7.5 | 7.0 | 7.0 | 2.7 | 2.5 |
| Midiron | 3.0 | 2.0 | 2.6 | 5.4 | 2.5 |
| LSD (0.05) | 2.5 | 2.7 | 2.3 | 2.3 | 3.2 |

†Greenup: 1 = brown, 5 = green; Color: 1 = brown, 9 = green; Quality: 1 = poor, 9 = best; Mole cricket damage: 1 = none, 9 = severe.
‡Experiment consisted of 2 replications of 2.7 × 2.7 m plots. Plots were mowed 3x each week at 12 mm height. Plots received 560 kg/ha 5-10-15 and 100 kg/ha N in March of each year and 50 kg/ha N in each June and August of each year. Plots were irrigated to prevent extreme stress. Test was sprayed with 2.2 kg/ha 2,4-D in March of each year. Test had 32 entries.
#Tifway 2 was included as one control in our earlier experiments because its was the most recent release and was expected to be more widely used than Tifway. This expectation was not realized. Data for Tifway in this table came from an adjacent replicated test with the same management conditions.

TABLE 3

1993 ratings† on bermudagrass test planted 5/18/92 at Tifton, GA‡.

| Cultivar | Quality 4/23 | 6/9 | 7/16 | 9/16 | 10/19 | 11/23 | 12/17 | x |
|---|---|---|---|---|---|---|---|---|
| Tift 94 | 7.0 | 7.5 | 7.0 | 7.5 | 7.0 | 7.5 | 7.5 | 7.2 |
| Tifdwarf | 8.5 | 8.0 | 9.0 | 9.0 | 9.0 | 7.0 | 8.0 | 8.4 |
| Tifgreen | 8.0 | 7.0 | 8.0 | 7.0 | 7.5 | 8.0 | 8.5 | 7.7 |
| LSD (0.05) | 1.4 | 1.2 | 1.1 | 0.9 | 1.4 | 1.1 | 1.0 | 1.2 |

| Cultivar | Color 11/23 | 12/17 | Mole Cricket Damage 10/20 | 12/17 |
|---|---|---|---|---|
| Tift 94 | 4.0 | 5.0 | 1.0 | 1.0 |
| Tifdwarf | 3.0 | 3.0 | 5.4 | 3.5 |
| Tifgreen | 3.5 | 4.0 | 5.4 | 3.5 |
| LSD (0.05) | 0.8 | 1.3 | 2.2 | 1.2 |

†Quality: 1 = poor, 9 = best.
Color: 1 = brown, 5 = green (on 12/17, 9 = green)
Mole cricket damage: 1 = none, 9 = severe
‡Mowed three times per week at 7 mm. Fertilized with 560 kg/ha 5-10-15 and 100 kg/ha N in March of each year. Fertilized with 50 kg/ha N in June and August of each year. Sprayed with 2.2 kg/ha 2-4,D in March of each year. Irrigated to prevent extreme stress. Test consisted of 2 replications of 2.8 × 2.5 m plots.

TABLE 4

Ratings on turf characteristics of bermudagrass cultivars established July, 1993 in 2.6 × 2.4 m plots (two replications).

| | Quality 1994 8/19 | 11/27 | 1995 5/25 | 7/11 | 10/4 | Color 12/31/94 | 7/11/94 | Mole Cricket Damage 10/4/95 |
|---|---|---|---|---|---|---|---|---|
| Tift 94 | 7.5 | 8.0 | 6.5 | 8.0 | 7.5 | 4.0 | 8.0 | 0.5 |
| Tifway | 7.5 | 8.0 | 6.5 | 7.5 | 7.0 | 4.0 | 8.0 | 0.5 |
| LSD (0.05) | 1.0 | 1.5 | 2.2 | 1.5 | 1.3 | 0.0 | 1.3 | 1.8 |

Ratings:

Quality: 1 = poor, 9 = best

Color: 1 = brown, 9 = dark green

Mole cricket damage: 0 = none, 5 = severe

Note: These entries were part of a 36-entry test. This test received 560 kg/ha 5-10-15 March and 50 kg/ha N monthly from May through August. Plots were irrigated to prevent moisture stress.

TABLE 5

1991 ratings† on bermudagrass cultivars at Stillwater, Oklahoma‡. (Test conducted by Joel Barber).

| Cultivar | Greenup 4/10 | 4/19 | Quality 7/10 |
|---|---|---|---|
| | % | | |
| MI22 | 80 | 100 | 7 |
| Tift 94 | 80 | 100 | 7 |
| MI53 | 50 | 70 | 5 |
| Tifgreen | Dead | Dead | Dead |

†Quality: 1 = poor, 9 = best
‡Planted June, 1990. Fertilized with 0.6 to 1.1 kg/ha N/1000 sq. ft. per month. Mowing height started at 19 mm and gradually reduced to 10 mm. Plots = single, 9.3 × 9.3 m plots.

TABLE 6

Ratings† on Midiron mutants at Lexington, KY‡. (Test conducted by A.J. Powell).

| Cultivar | % Cover 1991 May | July | Sept. | Quality 1992 | 1993 | Texture 9-24-92 | 1993 |
|---|---|---|---|---|---|---|---|
| | | | | x | | | |
| MI35 | 43 | 97 | 100 | 5.4 | 5.8 | 7 | 7.5 |
| Tift 94 | 63 | 98 | 100 | 6.3 | 6.2 | 7 | 7.3 |
| MI53 | 63 | 100 | 100 | 6.3 | 6.1 | 7 | 7.3 |
| Tifway 2 | 25 | 77 | 100 | 4.6 | 5.3 | 7 | 7.2 |
| LSD (.05) | 49 | 36 | 22 | 2.1 | 1.7 | | 1.0 |

†Quality: 1 = poor, 9 = best; Texture: 1 = coarse, 9 = fine
‡Planted July 15, 1991. Maintained at 19 mm.

TABLE 7

Ratings† on turf bermudagrass planted at Lake Wales, FL on 7-24-91. (Test conducted by Southern Turf Nurseries).

| | Rated in 3-25-93 | | |
|---|---|---|---|
| Cultivar | Density | Color | Quality |
| Tift 94 | 7.5 | 4.0 | 8.0 |
| Tifdwarf | 9.0 | 4.0 | 8.5 |
| Tifgreen | 9.0 | 3.5 | 9.0 |
| LSD (.05) | 1.0 | 0.8 | 1.3 |

Rated two weeks after last frost. Mowed once per week at 25 mm. Plots were 3.9 × 4.2 m, two replications. Density: 1 = open, 9 = dense; color: 1 = brown, 5 = green; Quality: 1 = poor, 9 = best. Test consisted of 12 cultivars.

TABLE 8

Ratings on turf characteristics of two bermudagrass cultivars established 6-30-94 in 2.7 × 2.7 m plots (2 replications)

| | | x | | |
|---|---|---|---|---|
| Characteristics | | Tift 94 | Tifway | LSD (0.05) |
| 1994 (date) | | | | |
| 1. Cover | (8-19)-% | 90 | 80 | 20 |
| 2. Color | (11-27) | 9.0 | 8.5 | 0.8 |
| | (12-31) | 4.0 | 4.0 | 0.6 |
| 1995 | | | | |
| 1. Quality | (5-25) | 7.5 | 8.0 | 1.2 |
| | (7-11) | 9.0 | 8.0 | 1.2 |
| | (10-4) | 6.5 | 5.5 | 1.3 |
| 2. Color | (7-11) | 8.5 | 9.0 | 1.0 |

Ratings:
Color: 1 = brown, 9 = dark green
Quality: 1 = poor, 9 = best
Note: These entries were part of a 107-entry test. Plots received 560 kg/ha 5-10-15 in march and 50 kg/ha N monthly from May through August. Plots were watered to prevent moisture stress.

TABLE 9

Ratings on turf characteristics of cultivars established as single 5 cm plugs on 7-12-91 at Fort Bluff, TN.

| | Quality | | Plant Diameter (cm) |
|---|---|---|---|
| | 11-7-92 | 10-11-93 | 11-7-92 |
| Tift 94 | 5.5 | 9.0 | 31 |
| Tifway | 6.5 | 9.0 | 36 |
| Tifway 2 | 4.5 | 7.5 | 39 |
| LSD (0.05) | 3.8 | 3.8 | 41 |

Quality: 1 = poor, 9 = best
Note: This was part of a 20-entry test. Variable winter survival for some entries resulted in a high coefficient of variability and their high LSDs. Plots received 560 kg/ha 5-10-15 and 100 kg/ha N yearly. Plots were not irrigated.

TABLE 10

Morphological characteristics of three bermudagrass cultivars planted as 10 cm plugs in 20 cm pots in the greenhouse on 10-5-95 and measured 11-9-95.

| | Cultivars | | | |
|---|---|---|---|---|
| | Tift 94 | Midiron | Tifway | LSD (0.05) |
| Shoot height (cm) | 10.7 | 20.6 | 14.9 | 1.2 |
| Leaf length (cm) | 5.6 | 10.7 | 7.0 | 0.5 |
| Leaf width (mm) | 1.2 | 2.2 | 1.4 | 0.1 |
| Number of shoots | 475 | 87 | | 95 |

Each cultivar had six replications (pots). Fifteen observations were made per replication for leaf length and width. Plants were not defoliated.

TABLE 11

Morphological characteristics of three bermudagrass cultivars planted in the field in 1992, mowed weekly at 3 cm, and rated 10-20-95.

| | Cultivars | | |
|---|---|---|---|
| | Midiron | Tift 94 | Tifway |
| Internode length (cm) | | | |
| Horizontal stolons | 2.5 ± 1.1 | 1.2 ± 0.5 | 1.5 ± 0.4 |
| Vertical shoots | 1.0 ± 0.5 | 0.6 ± 0.3 | 0.8 ± 0.3 |
| Leaf length (cm) | 2.0 ± 0.5 | 1.3 ± 0.4 | 1.6 ± 0.4 |
| Leaf width (mm) | 1.9 ± 0.8 | 1.2 ± 0.2 | 1.2 ± 0.2 |

*117 observations for each internode length mean. 78 observations for each leaf length and width mean. Plots received 560 kg/ha 5-10-15 and 100 kg/ha N yearly. Plots received only natural rainfall.

TABLE 12

Morphological characteristics of three unmowed bermudagrass cultivars planted as 5 cm plugs on 9-8-95 in the field and rated 10-20-95.

| | Cultivars | | |
|---|---|---|---|
| | Tift 94 | Midiron | Tifway |
| Internode length (mm)† | | | |
| 1st | 25 ± 5 | 24 ± 4 | 26 ± 5 |
| 2nd | 25 ± 5 | 25 ± 5 | 27 ± 5 |
| 3rd | 24 ± 5 | 25 ± 5 | 27 ± 4 |
| 4th | 23 ± 6 | 23 ± 5 | 26 ± 4 |
| 5th | 22 ± 5 | 22 ± 6 | 26 ± 4 |
| Shoot number at node‡ | | | |
| 1st | 1.2 ± 0.5 | 1.0 ± 0.5 | 1.2 ± 0.5 |
| 2nd | 1.8 ± 0.9 | 1.2 ± 0.5 | 1.9 ± 0.7 |
| 3rd | 2.4 ± 0.9 | 1.4 ± 0.7 | 2.3 ± 0.1 |
| 4th | 2.4 ± 1.2 | 1.3 ± 0.7 | 2.6 ± 1.1 |
| 5th | 2.7 ± 1.2 | 1.5 ± 0.8 | 2.4 ± 1.0 |
| Leaf length (cm) | 1.4 ± 0.3 | 1.9 ± 0.4 | 1.7 ± 0.4 |
| Leaf width (mm) | 1.7 ± 0.3 | 2.3 ± 0.3 | 1.7 ± 0.3 |

Each mean based on 50 or more observations. Plots received 560 kg/ha 5-10-15 and 50 kg/ha N at planting. Plots were irrigated to prevent moisture stress.
†Begins with first fully extended internode from growing point end of stolon.
‡Begins node of first fully extended internode at opposite end of growing point of stolon.
Note: Stolons were in a juvenile growth stage.

What is claimed is:

1. A new and distinct cultivar of Bermudagrass plant, substantially as herein shown and described, distinguished by the fine textures of the leaf blade, short internodes, and improved color which produces a low growing turf with improved density and quality.

* * * * *